United States Patent [19]

Liu et al.

[11] 4,299,974

[45] Nov. 10, 1981

[54] PROCESS FOR PREPARING N-PROTECTED 2-AMINOETHANETHIOL

[75] Inventors: Thomas M. H. Liu; Ichiro Shinkai, both of Westfield; Meyer Sletzinger, North Plainfield, all of N.J.

[73] Assignee: Merck & Co., Inc., Rahway, N.J.

[21] Appl. No.: 159,982

[22] Filed: Jun. 16, 1980

[51] Int. Cl.³ .................. C07C 102/00; C07C 101/18
[52] U.S. Cl. .................................. 560/148; 556/426; 564/142; 564/143; 564/175; 564/182; 564/192
[58] Field of Search .................. 560/148; 556/426; 564/142, 143, 192, 175, 182

[56] References Cited

PUBLICATIONS

Kricheldorf, Liebigs Ann. Chem., 1973, 772–792.
Abel, J. Chem. Soc. 1960, pp. 4406–4409.
Birkofer et al., Newer Methods of Preparation, Org. Chem., vol. 5, Academic Press, N.Y., N.Y., 1968, pp. 211–212.

*Primary Examiner*—Arthur P. Demers
*Attorney, Agent, or Firm*—James A. Arno; Hesna J. Pfeiffer

[57] ABSTRACT

Disclosed is a process for preparing N-protected 2-aminoethanethiol which proceeds via the silyl covered sulfur intermediate:

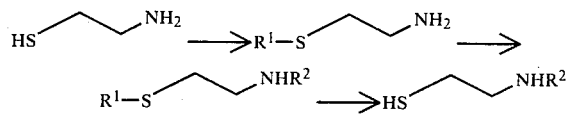

wherein $R^1$ is triorganosilyl and $R^2$ is a readily removable N-protecting group.

3 Claims, No Drawings

PROCESS FOR PREPARING N-PROTECTED 2-AMINOETHANETHIOL

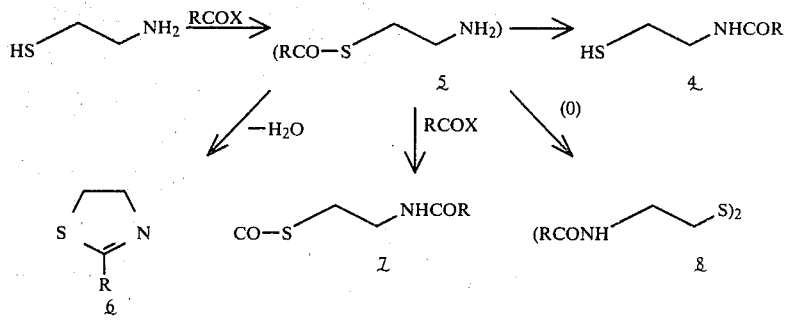

BACKGROUND OF THE INVENTION

This invention relates to a process for preparing N-protected 2-aminoethanethiol (4). The process may be summarized by the following scheme:

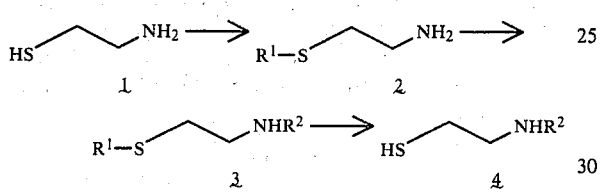

wherein $R^1$ is triorganosilyl and $R^2$ is a readily removable N-protecting group. Particularly preferred triorganosilyl protecting groups $R^1$ and N-protecting groups $R^2$ are described below, as are preferred conditions of reaction.

The N-protecting 2-aminoethanethiols (4) so prepared are useful in the synthesis of thienamycin. The utility of 4 in this manner is known. See, for example, European patent application No. 79101307.1 (published Feb. 20, 1980); publication number 007973/A1. This publication is incorporated herein by reference for the purpose of defining the utility of 4, which utility may be summarized by the following steps:

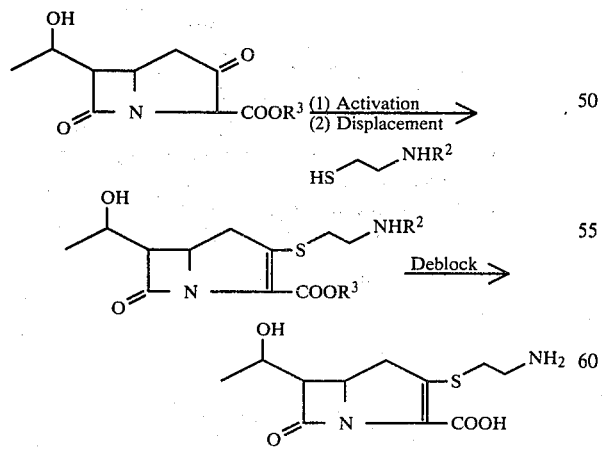

The unexpected advantage of the instant process is that it provides 4 in substantially pure form. Conventional procedures, when applied to the synthesis of 4, yield an annoying mixture of products, from which 4 is separated only with difficulty and expense. The principal courses of such conventional schemes are demonstrated by the following set of reactions:

wherein the acylating agent RCOX (X is chloro), which establishes the N-acyl protecting group RCO, is embraced by the previously defined N-protecting group $R^2$.

($R^2$ is CR.)

The intermediate S-acylated species 5 is known to transfer the acyl group from sulfur to nitrogen to form 4. However, this S-acylated intermediate does participate in the undesired reactions leading to formation of the cyclized 6, bis-acylated 7 and oxidation side 8 products.

DETAILED DESCRIPTION OF THE INVENTION

Reference is made to the previously given scheme 1→2→3→4. In words, initial reactant 1, preferably as an acid addition salt such as the hydrochloride, in a solvent such as acetonitrile, N,N-dimethylformamide, dichloromethane, tetrahydrofuran or the like in the presence of 2 to 3 equivalents of a base such as diisopropylethylamine, trimethylamine, pyridine, or the like is contacting with 1 to 1.5 equivalents of a triorganosilylating agent such as trimethylchlorosilane, dimethyl-t-butylchlorosilane, dimethylbenzylchlorosilane, dimethylphenylchlorosilane or the like. It will be noted that there is no criticality as to the identity of the base in this reaction system; however, triorganoamines, pyridine and substituted pyridines are preferred because of their compatibility with the solvent system. Likewise, there is no criticality as to the precise identity of the solvent, any solvent being suitable which permits the intended course of reaction. Further, it should be noted that while triloweralkylsilyl protecting groups are preferred, the requirement here is simply that the silyl function be successfully established and removed consistent with the overall production of desired product 4.

The reaction 2→3 is preferably an acylation, and may be achieved by any of a variety of well known acylation procedures. The resulting N-acyl protecting group $R^2$, or

—CR, may be selected from those well known in the art. Preferred values for $R^2$ include,

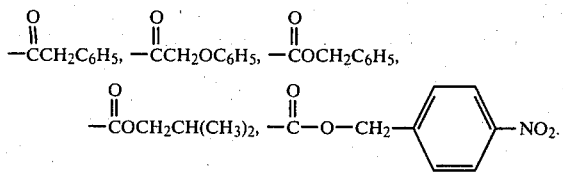

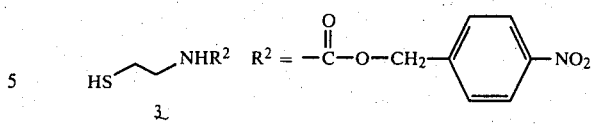

Preferred acylating agents to establish these N-protecting groups $R^2$ are the corresponding acid halides. RCOX wherein X is chloro or bromo. Other acylating agents may also be employed, such as any activated carboxylic acid, for example, phosphate, an imidazolide, an acid anhydride, or a mixed anhydride. Typically, the acylation reaction is conducted in any solvent in which the reactants are suitable and substantially inert, for example, polar solvents such as water, alcohols and polar organic solvents in general such as dimethylformamide (DMF), hexamethylphosphoramide (HMPA), acetone, dioxane, tetrahydrofuran (THF), acetonitrile, aqueous mixtures of the above, as well as halogenated solvents such as methylene chloride and chloro, for example; the reaction mixture in the presence of the acylating agent of choice, RCOX, in the presence of a suitable organic or inorganic acceptor base such as sodium hydrogen carbonate, triethylamine, diisopropylethylamine, pyridine or the like; typically, the reaction is conducted at a temperature of from $-20°$ to $100°$ C., but is preferably at a temperature in the range of $-8°$ to $25°$ C.; the reaction is complete in a few minutes to 1 hour.

The deblocking reaction $\underline{3}\rightarrow\underline{4}$, which removes the triorganosilyl protecting group $R^1$, is accomplished by treating $\underline{3}$ in a solvent such as tetrahydrofuran, acetonitrile, DMF or the like with water, dilute aqueous acid such as hydrochloric acid or the like, or a catalytic amount of tetraalkyl ammonium fluoride.

In the foregoing word description, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite precise schemes; however, it is to be understood that the purpose of this recitation is to further illustrate the claimed process and not to impose any limitations.

All temperatures are in °C.

EXAMPLE 1

Preparation of $\underline{3}$:

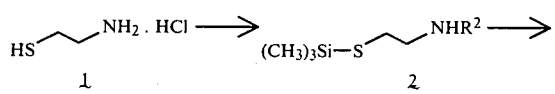

To 2-aminoethanethiol hydrochloride (1.136 g, 10 mm) in 15 ml CH$_3$CN under nitrogen at 0° C. is added diisopropylethylamine (3.99 ml, d=0.742, 23 mm) in 1 ml CH$_3$CN comprising a trace of imidazole. The mixture is stirred for 5 minutes and then trimethylchlorosilane (1.64 ml, d=0.856, 13 mm) in 1 ml CH$_3$CN is slowly added over two minutes; the mixture is allowed to warm to room temperature for 15 minutes and then cooled again to 0° C.; whereupon diisopropylethylamine (1.73 ml, 10 mm) is added followed by the addition of p-nitrobenzylchloroformate (2.16 g, 10 mm). The mixture is stirred at room temperature (22° C.) for 1 hour. The reaction mixture is returned to 0° C. and 5 ml of water are added. The acetonitrile is removed; an equivalent volume of water is added and the mixture is extracted three times with 20 ml CH$_2$Cl$_2$, washed with dilute aqueous HCl followed by dilute sodium hydrogen carbonate and the residue is evaporated to dryness to yield 2.48 g of desired product $\underline{3}$ (96.8% yield) m.p. 66°–68° C.

EXAMPLE 2

Preparation of

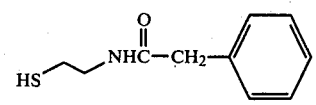

Following the procedure of Example 1 except substituting an equivalent amount of phenylacetylchloride for the p-nitrobenzylchloroformate there is obtained the title compound; 95% yield, m.p. 50°–52° C.

EXAMPLE 3

Preparation of

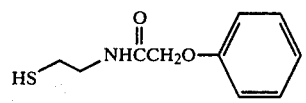

Following the procedure of Example 1 except substituting an equivalent amount of phenoxyacetylchloride for the p-nitrobenzylchloroformate the title compound is obtained; 85% yield, m.p. 28°–30° C.

EXAMPLE 4

Preparation of

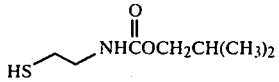

Following the procedure of Example 1 except substituting an equivalent of isobutylchloroformate for the p-nitrobenzylchloroformate, the title product is obtained in 96% yield.

Following the procedures of Examples 1-4, equivalent results are obtained when the silylating agent trimethylchlorosilane is replaced in an equivalent amount by dimethyl-t-butylchlorosilane, dimethyl benzylchlorosilane, dimethyl phenylchlorosilane, respectively.

What is claimed is:

1. A process for preparing:

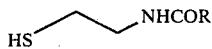

comprising the steps of treating 2-aminoethanethiol in the presence of base with a silylating agent followed by treating with acylating agent RCOX to yield:

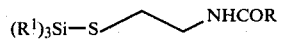

followed by hydrolysis; wherein X is chloro or bromo and

is a readily removable N-protecting group wherein R is selected from the group consisting of:

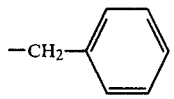

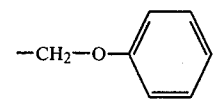

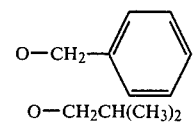

$-O-CH_2CH(CH_3)_2$

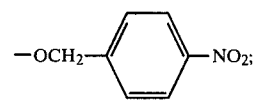

and $R^1$ is independently chosen from alkyl having from 1-6 carbon atoms, phenyl and phenylalkyl having from 7-12 carbon atoms.

2. A process according to claim 1 wherein $(R^1)_3Si-$ represents a trialkylsilyl group.

3. A process according to claim 2 wherein the trialkylsilyl is selected from the group consisting of:
—Si(CH$_3$)$_3$
—Si(CH$_3$)$_2$[C(CH$_3$)$_3$]
—Si(CH$_3$)$_2$ (CH$_2$CH$_3$)
—Si(CH$_3$)$_2$ (CH$_2$C$_6$H$_5$).

* * * * *